United States Patent
Laroche et al.

(10) Patent No.: US 11,059,764 B2
(45) Date of Patent: Jul. 13, 2021

(54) HYBRID PROCESS FOR PRODUCING HIGH-PURITY PARA-XYLENE WITH TOLUENE SOLVENT

(71) Applicants: IFP Energies Nouvelles, Rueil-Malmaison (FR); Arkema France, Colombes (FR)

(72) Inventors: Catherine Laroche, Charly (FR); Morgane Josserand, Lyons (FR); Danielle Richard, Lyons (FR); Javier Perez-Pellitero, Lyons (FR); Ludivine Bouvier, Orthez (FR)

(73) Assignees: IFP Energies Nouvelles, Rueil-Malmaison (FR); Arkema France, Colombes (FR)

( * ) Notice: Subject to any disclaimer, the term of this patent is extended or adjusted under 35 U.S.C. 154(b) by 0 days.

(21) Appl. No.: 16/642,725

(22) PCT Filed: Sep. 4, 2018

(86) PCT No.: PCT/EP2018/073734
§ 371 (c)(1),
(2) Date: Feb. 27, 2020

(87) PCT Pub. No.: WO2019/043249
PCT Pub. Date: Mar. 7, 2019

(65) Prior Publication Data
US 2020/0223770 A1    Jul. 16, 2020

(30) Foreign Application Priority Data

Sep. 4, 2017  (FR) ...................................... 1758129

(51) Int. Cl.
*C07C 7/00* (2006.01)
*B01D 9/00* (2006.01)
(Continued)

(52) U.S. Cl.
CPC ............ *C07C 7/005* (2013.01); *B01D 9/0045* (2013.01); *B01D 15/1807* (2013.01);
(Continued)

(58) Field of Classification Search
CPC .. C07C 7/005; C07C 7/13; C07C 7/14; B01D 9/0045; B01D 15/1807; B01D 15/1871;
(Continued)

(56) References Cited

U.S. PATENT DOCUMENTS 2,985,589 A    5/1961  Broughton et al.
3,177,265 A    4/1965  Lammers
(Continued)

FOREIGN PATENT DOCUMENTS

CN    103508837 A    1/2014
EP    0531191 A1     3/1993
(Continued)

OTHER PUBLICATIONS

International Search Report and Written Opinion for International Application No. PCT/FR2018/073734, dated Nov. 19, 2018, 10 pages.

*Primary Examiner* — Ali Z Fadhel
(74) *Attorney, Agent, or Firm* — RatnerPrestia (57) ABSTRACT

Provided is a hybrid process for producing high-purity para-xylene from a feedstock of aromatic hydrocarbon isomer fractions having 8 carbon atoms, in a liquid phase. The process includes a liquid chromatography separation step and a crystallization step of the para-xylene from the purified stream of para-xylene obtained at the separation step.

15 Claims, 4 Drawing Sheets

(51) Int. Cl.
| | |
|---|---|
| *B01D 15/18* | (2006.01) |
| *B01J 20/12* | (2006.01) |
| *B01J 20/18* | (2006.01) |
| *B01J 20/28* | (2006.01) |
| *B01J 20/282* | (2006.01) |
| *B01J 20/30* | (2006.01) |
| *C07C 7/13* | (2006.01) |
| *C07C 7/14* | (2006.01) |

(52) U.S. Cl.
CPC ......... *B01D 15/1871* (2013.01); *B01J 20/12* (2013.01); *B01J 20/18* (2013.01); *B01J 20/282* (2013.01); *B01J 20/28052* (2013.01); *B01J 20/3028* (2013.01); *B01J 20/3042* (2013.01); *B01J 20/3078* (2013.01); *B01J 20/3085* (2013.01); *C07C 7/13* (2013.01); *C07C 7/14* (2013.01); *B01D 2009/0086* (2013.01); *B01J 2220/42* (2013.01); *B01J 2220/52* (2013.01)

(58) Field of Classification Search
CPC ... B01D 2009/0086; B01J 20/12; B01J 20/18; B01J 20/28052; B01J 20/282; B01J 20/3028; B01J 20/3042; B01J 20/3078; B01J 20/3085; B01J 2220/42; B01J 2220/52
See application file for complete search history.

(56) References Cited

U.S. PATENT DOCUMENTS

| | | | |
|---|---|---|---|
| 3,467,724 A | | 9/1969 | Laurich |
| 3,558,730 A | | 1/1971 | Neuzil |
| 3,558,732 A | | 1/1971 | Neuzil |
| 3,663,638 A | | 5/1972 | Neuzil |
| 3,878,127 A | | 4/1975 | Rosback |
| 4,351,981 A | * | 9/1982 | Smolin .............. C07C 7/13 585/828 |
| 4,402,832 A | | 9/1983 | Gerhold |
| 4,409,819 A | * | 10/1983 | Smolin .............. C07C 7/13 73/61.43 |
| 4,415,481 A | * | 11/1983 | Smolin ............ B01J 29/082 502/62 |
| 4,439,535 A | * | 3/1984 | Smolin ............ B01J 20/18 502/62 |
| 4,498,991 A | | 2/1985 | Oroskar |
| 4,615,994 A | * | 10/1986 | Smolin ............ B01J 20/186 502/62 |
| 5,284,992 A | | 2/1994 | Hotier et al. |
| 5,401,476 A | * | 3/1995 | Hotier .............. C07C 7/005 422/222 |
| 8,530,367 B2 | | 9/2013 | Bouvier et al. |
| 8,735,643 B2 | | 5/2014 | Bouvier et al. |
| 9,050,581 B2 | | 6/2015 | Bouvier et al. |
| 9,919,289 B2 | | 3/2018 | Bouvier et al. |
| 2011/0124942 A1 | * | 5/2011 | Bouvier .............. C07C 29/76 585/820 |
| 2011/0184165 A1 | * | 7/2011 | Bouvier ............ B01J 20/28069 536/127 |

FOREIGN PATENT DOCUMENTS

| | | |
|---|---|---|
| EP | 2237678 A2 | 10/2010 |
| EP | 2237877 A2 | 10/2010 |
| FR | 2681066 A1 | 3/1993 |
| FR | 2693187 A1 | 1/1994 |
| FR | 2903978 A1 | 1/2008 |
| FR | 2925366 A1 | 6/2009 |
| FR | 2925367 A1 | 6/2009 |
| FR | 3028430 A1 | 5/2016 |
| WO | 2016075281 A1 | 5/2016 |

\* cited by examiner

HYBRID PROCESS FOR PRODUCING HIGH-PURITY PARA-XYLENE WITH TOLUENE SOLVENT

CROSS-REFERENCE TO RELATED APPLICATIONS

This is the national phase of International Application No. PCT/EP2018/073734, filed 4 Sep. 2018, which claims priority to French Application No. 1758129, filed 4 Sep. 2017. The disclosure of each of these applications is incorporated herein by reference in its entirety for all purposes.

FIELD OF THE INVENTION

The invention relates to a process for producing high-purity paraxylene from a feedstock of aromatic hydrocarbons containing isomers having 8 carbon atoms. More specifically, the invention concerns a hybrid process comprising a paraxylene adsorption step and a crystallization step, using toluene as common solvent and a particular faujasite zeolite adsorbent containing barium.

BACKGROUND OF THE INVENTION

The market for high-purity paraxylene is considered to be a fast-expanding market, the major outlets being the production of terephthalic acid (PTA), obtained via oxidation of paraxylene, used to produce polyester fibres for clothing and polyethylene-terephthalate resins and films (PET).

High-purity paraxylene is produced via recovery of xylenes according to a process called "C8-aromatics loop" including steps of separation (removal of heavy compounds in the "xylene column", extraction of paraxylene) and isomerization of the xylenes. The extraction of high-purity paraxylene via selective adsorption is well known in the prior art. The technological background describing the production of paraxylene of very high purity is illustrated in patent FR 2 681 066 (Institut Francais du Pétrole) and is based on the separation of paraxylene from a feedstock of aromatic hydrocarbons essentially having 8 carbon atoms in an adsorption unit, via contact with a bed of zeolitic adsorbent in the presence of a suitable desorption solvent (desorbent).

For this type of separation, a family of adsorption processes and associated systems is used, known as chromatographic separation processes and systems or "simulated moving bed" or "simulated counter-current", which shall be termed hereafter as "SMB" processes and systems similar to those described in patents U.S. Pat. Nos. 2,985,589, 4,402,832 and 4,498,991 and which inter alia apply to C8 aromatic fractions.

With this type of process, a stream of extract is obtained containing desorption solvent and essentially paraxylene having very high purity, generally higher than 99.5% and typically higher than 99.7%, and a stream of raffinate containing desorbent, metaxylene, ortho-xylene, ethylbenzene and practically no paraxylene.

Another known method for separating paraxylene from a feedstock of aromatic hydrocarbons essentially having 8 carbon atoms consists in carrying out a fractionated crystallization. The processes described in patents U.S. Pat. Nos. 3,177,265 and 3,467,724 use two crystallization steps: the first step is performed between −70° C. and −50° C., and the second is in the region of −10° C. The main disadvantages of this method are a limited maximum recovery rate per pass of about 60% on account of the presence of eutectics between paraxylene and the other C8 aromatic isomers, and high energy cost related to the heat schedule of the first step.

Patent FR 2 681 066 describes a hybrid process combining a first separation step via liquid chromatography of "SMB" type with a second crystallization step.

The advantages of such combination, compared with an exclusively chromatographic process of SMB type, lie in the fact that the paraxylene produced in the extract at the liquid chromatography separation step is of low purity, typically 75 to 98%, which allows:
  considerably improved productivity (volume of feedstock treated per volume of adsorbent and per hour);
  lower ratio of desorption solvent flow rate to injected feedstock flow rate;
  the use of a smaller number of separate beds.

The extract produced at this first step contains paraxylene that is already concentrated and then purified at the second crystallization step to reach very high purity of at least 99.3%, and typically at least 99.7%. If the input paraxylene content for crystallization is between 85 and 90%, the crystallization temperature is between −5° C. and −15° C. This temperature level typically corresponds to the temperature level of the second step in a crystallization separation process, the first typically being operated at between −70 and −50° C. Therefore, the advantages of said combination compared with an exclusively crystallization process are:
  avoidance of prohibitive operating costs associated with the first crystallization step;
  the reaching of paraxylene recovery levels (yield) of at least 98%.

This combination therefore allows both CAPEX savings (capital expenditure) on the chromatographic section through the reduced number of beds and high productivity, as well as OPEX savings (operating expenditure i.e. utility expenses) through a reduced amount of desorbent on the chromatographic section and a crystallization section limiting frigories.

Patent CN 103508837 also proposes a hybrid process of this type combining a chromatographic separation step of SMB type and a crystallization step. In the described process, the washing solvent for the crystals is toluene, whilst the desorption solvent is diethylbenzene.

Patent FR 2 681 066 describes that the desorption solvent and washing solvent can be a solvent having a boiling point lower than that of the feedstock, e.g. toluene, or higher than that of feed stock e.g. cumene, but also that the desorption solvent can be a solvent having a boiling point higher than the feedstock such as para-diethylbenzene and the washing solvent can be a solvent having a boiling point lower than that of the feedstock, such as toluene.

Patent FR 2 681 066 also shows that adequate selection of the washing solvent and desorption solvent allows a synergy to be set up between the chromatography and crystallization steps when said solvent is common to the two steps, by omitting a distillation unit. Toluene has been described as desorption solvent for the separation of xylenes with adsorbents chiefly composed of X- or Y-zeolites having exchangeable sites occupied by alkaline or alkaline-earth cations. Also, in fractionated crystallization processes, it is known to use toluene as washing solvent of paraxylene crystals.

To obtain good performance in a hybrid process combining adsorption and crystallization, it is necessary to select an adsorbent that is efficient for separation of paraxylene via liquid chromatography in the presence of a suitable desorption solvent, allowing optimal operation of the crystallization step to obtain paraxylene of high purity whilst minimising costs.

In particular, to obtain good performance at the adsorption step, determinant for efficacy of the subsequent crystallization step, the adsorbent to be used for chromatographic separation must by efficient at selectively adsorbing paraxylene in a mixture of aromatic hydrocarbons, and must also be efficiently regenerated by the desorption solvent. More specifically, if the selected common solvent is toluene, the adsorbent must particularly be capable of efficiently separating paraxylene from the other C8 isomers, in particular with high selectivity between paraxylene and metaxylene (e.g. of at least 3) and must be efficiently regenerated by toluene as desorption solvent.

It is known in the prior art that zeolite adsorbents comprising at least faujasite zeolite (FAU) of X or Y type and also comprising sodium cations, barium, potassium or strontium ions, alone or in a mixture, are efficient for selectively adsorbing paraxylene in a mixture of aromatic hydrocarbons (U.S. Pat. Nos. 3,558,730, 3,558,732, 3,663,638 and 3,878,127).

Patent FR 2 681 066 specifies that when the desorption solvent is toluene, the preferred zeolite is Y-type zeolite exchanged both with barium and potassium, whereas when the desorption solvent is para-diethylbenzene (PDEB) the preferred zeolite is X-type zeolite almost entirely exchanged with barium.

However, Y-type zeolite exchanged both with barium and potassium, the use of which is recommended in patent FR 2 681 066 for SMB in the presence of toluene as desorption solvent, does not allow obtaining a satisfactory selectivity between paraxylene and metaxylene. In fact, the selectivity obtained with this zeolite between paraxylene and metaxylene is in the region of 2.5.

Surprisingly, adsorbents mostly containing FAU zeolite, comprising barium and having a lattice parameter «a» higher than 25.100 Å (i.e. 2.5100 nm) such that the barium content of the adsorbent expressed as weight of barium oxide BaO relative to the total weight of the adsorbent is between 30% and 41%, used in a hybrid process comprising an adsorption step and a crystallization step, in the presence of toluene that is both desorption solvent and washing solvent, allow the use of a smaller quantity of desorbent to regenerate the adsorbent, while obtaining high selectivity (α) for paraxylene in relation to metaxylene (PX/MX) and in relation to ethylbenzene (PX/EB) (in particular PX/MX selectivity >3 and PX/EB selectivity >2.4).

Said «a» lattice parameter is measured on the final adsorbent after exchange with barium.

The invention does not exclude the presence of other alkaline or alkaline-earth cations in a small amount or in traces, typically in a content of less than 5% by weight of oxide relative to the total weight of the adsorbent.

SUMMARY OF THE INVENTION

The invention relates to a hybrid process for producing high-purity para-xylene from a feedstock of aromatic hydrocarbon isomer fractions having 8 carbon atoms, in liquid phase, comprising:
  a) a separation step of para-xylene via simulated countercurrent adsorption using a zeolitic adsorbent and a desorption solvent, said adsorbent comprising:
    at least one majority zeolite of faujasite type having a lattice parameter «a» higher than 25.100 Å,
    barium such that the content of barium oxide BaO is comprised between 30% and 41% by weight, limits included, relative to the total weight of the adsorbent,
    to obtain a stream of purified paraxylene
  b) a crystallization step of the paraxylene from the purified stream of paraxylene obtained at the separation step, at a temperature comprised between 0 and −25° C., followed by washing of the crystals with a washing solvent, to obtain paraxylene of high purity,
  the desorption solvent at the separation step and the washing solvent at the crystallization step being toluene.

The adsorbent may comprise an LSX zeolite.

In one embodiment, the outer surface of said zeolite adsorbent, measured by nitrogen adsorption, is less than 100 $m^2 \cdot g^{-1}$.

The adsorbent may comprise a mixture of faujasite-type zeolites, preferably a mixture of an X-type and LSX zeolite, the LSX zeolite being the majority component.

Preferably, the barium oxide content is comprised between 33 and 41% limits included, more preferably between 33 and 38% limits included, relative to the total weight of the adsorbent. The temperature at the crystallization step is advantageously in comprised between −5° C. and −15° C.

The crystal wash ratio is comprised between 0.8 and 2 volumes of toluene per volume of paraxylene crystals.

The number of beds at the separation step is advantageously comprised between 4 and 24, preferably between 8 and 12.

In one embodiment of the process of the invention, the separation step via adsorption is conducted with a number of beds of between 4 and 24, a number of zones of at least 4, at a temperature comprised between 100° C. and 250° C., at pressure between toluene bubble point pressure at the processing temperature and 3 MPa, a cycle time corresponding to the time interval between two injections of desorbent into a given bed of between 4 and 18 min, a flow rate ratio of desorbent to feedstock of 0.7 to 2.5, a recycle ratio (ratio between the mean flow rate in the zones, weighted for the number of beds in each zone, and the feed flow rate) comprised between 2 and 12.

Preferably, the separation step via adsorption is conducted at a temperature comprised between 150° C. and 180° C.

Preferably, the separation step via adsorption is conducted with a recycle ratio (ratio between the mean flow rate in the zones, weighted for the number of beds in each zone, and the feed flow rate) comprised between 2.5 and 4.

The adsorbent used in the process of the invention can be obtained with any method known to persons skilled in the art, and in particular with one of the methods described in patent applications EP2237878, EP2237877 and WO2016/075281.

Advantageously, the adsorbent is prepared according to the following steps:
  a) mixing crystals of faujasite zeolite in powder form of desired particle size, in the presence of water, with at least one binder containing a clay or mixture of clays comprising at least 80% by weight of zeolitizable clay and optionally a silica source;
  b) forming the mixture obtained at a) to produce aggregates, followed by drying and optionally a screening and/or cyclonic separation step;
  c) calcining the aggregates obtained at b) at a temperature preferably in the range of 500° C. to 600° C.;
  d) optionally zeolitizing the binder by contacting the calcined aggregates obtained at step c) with an alkaline basic aqueous solution followed by washing;

e) ion exchange of the zeolitic aggregates containing LSX, or X and LSX zeolite obtained at c) or d) with barium ions, followed by washing and drying of the product thus treated;

f) heat activation of the aggregates exchanged at step e), for example at a temperature in the range of 200 to 300° C.

BRIEF DESCRIPTION OF THE FIGURES

FIG. 1: (A) Diffractogram obtained with X-ray diffraction on adsorbents C (comparative) and F (conforming to the invention) with zoom on the split peak at 35°. (B) Diffractogram obtained with X-ray diffraction on adsorbents C (comparative) and F (conforming to the invention) and zoom on the split peak at 35° (offset).

DETAILED DESCRIPTION OF THE INVENTION

In the remainder of the description, by X-type zeolite it is meant a zeolite of faujasite type having a Si/Al atomic ratio comprised between 1.15 limit excluded and 1.5 limit included.

By LSX zeolite (Low Silica X) it is meant a zeolite of faujasite type with low silica content having a Si/Al atomic ratio close to 1, more specifically comprised between 1 and 1.15, limits included.

Adsorbents

The adsorbents used in the hybrid process of the invention contain at least one FAU zeolite having an «a» lattice parameter (cubic lattice such that a=b=c) determined by XRD strictly higher than 25.100 Å.

They may contain one or more other FAU zeolites but in this case the FAU zeolite(s) having a lattice parameter strictly higher than 25.100 Å are in majority. By majority zeolite(s) it is meant zeolites representing a weight proportion of at least 50% relative to all FAU zeolites. When the adsorbent contains several FAU zeolites, determination of the majority zeolite of FAU type is performed on the XRD signal corresponding to 35°±0.6° 2θ. When several FAU zeolites are present, the signal under consideration is characterized by a split peak, the left-hand peak corresponding to the zeolite having the highest lattice parameter. By majority zeolite it is then meant the zeolite having a surface area contribution that is strictly greater than 50% of the total surface area of the split peak, preferably strictly greater than 51%, more preferably strictly greater than 55%, and typically strictly greater than 60%.

Measurement of contribution in terms of surface area is performed on the final adsorbent after exchange with barium. If needed, and to improve the accuracy of determination of the contribution of each zeolite, a peak deconvolution method (available in XRD peak analysis tools) can be applied. In one particularly preferred embodiment, the proportion of zeolites other than FAU is always less than 10%.

The invention does not exclude the presence of other alkaline or alkaline-earth cations in a small quantity or in traces, typically in a content of less than 5% by weight of oxide relative to the total weight of the adsorbent.

The preferred adsorbents in the invention are the following: adsorbents comprising an LSX zeolite, adsorbents comprising an LSX zeolite having hierarchised porosity or high outer surface i.e. an outer surface of the adsorbent comprised between 20 and 100 $m^2/g$, or adsorbents comprising a mixture of an X zeolite and LSX zeolite, the LSX zeolite being in majority in the meaning described above.

The zeolitic adsorbents used in the present invention can be obtained by any technique known to skilled persons, in particular by one of the methods described in patent applications EP2237878, EP2237877 and WO2016/075281.

The zeolitic adsorbents used in the present invention are advantageously obtained in particular according to a preparation such as described in the foregoing:

a) mixing crystals of faujasite zeolite e.g. crystals of LSX zeolite or crystals of X and LSX zeolite in powder form having the desired particle size, in the presence of water, with at least one binder containing a clay or mixture of clays comprising at least 80%, preferably at least 90%, more preferably at least 95% by weight of zeolitizable clay and optionally a silica source;

b) forming the mixture obtained at a) to produce aggregates, followed by drying and optionally a screening and/or cyclonic separation step;

c) calcining the aggregates obtained at b) at a temperature preferably in the range of 500° C. to 600° C.;

d) optional zeolitizing of the binder by contacting the calcined aggregates obtained at step c) with an alkaline basic aqueous solution, followed by washing;

e) ion exchange of the zeolitic aggregates containing LSX zeolite or X and LSX obtained at c) or d) with barium ions, followed by washing and drying of the product thus treated;

f) heat activation of the product obtained at step e), preferably at a temperature in the range of 200 to 300° C.

The forming step b) allows to obtain zeolitic aggregates having sufficient mechanical strength for use thereof in a simulated moving bed process to separate xylenes. However, the presence of binder reduces the proportion of active material for adsorption (zeolites LSX and X).

The optional zeolitizing step d) of the binder therefore allows all or part of the binder to be converted to active material for adsorption (zeolites LSX and X) in order to obtain binder-free aggregates i.e. no longer comprising a non-zeolitic phase (in an amount of typically less than 2%) or aggregates with scarce binder content i.e. comprising little (amount of typically between 2 and 5%) non-zeolitic phase (generally residual non-zeolitized binder or any other amorphous phase after zeolitization) in the final aggregates, while maintaining mechanical strength. The level of non-zeolitic phase (i.e. the non-zeolitized residual binder forming an inert amorphous phase in the meaning of adsorption, after zeolitization) in the final aggregate can be quantified by reference to an adsorbent composed solely of zeolite in powder form, from adsorption measurements or from X-ray diffraction peak intensities (XRD). The reference zeolite selected for quantification via X-ray diffraction (XRD) is the zeolite used at step a) of the method for preparing the adsorbent, and subjected to the same ion exchange.

The crystals of X-type or LSX zeolite derived from zeolitizing the binder (converting the binder to zeolite) are generally of smaller diameter than the initial crystals. Therefore, in the final aggregates the crystals having a mean diameter less than or equal to 7 µm, preferably comprised between 0.1 and 4 µm, and more preferably from 0.1 to 3 µm, conventionally exhibit single-mode particle size distribution, but it would remain within the scope of the invention if the diameter distribution of the crystals was multi-modal, and in particular bimodal, owing to the presence of the population of crystals derived from zeolitization of the binder.

Measurement of the lattice parameter «a», performed on the final adsorbent after exchange with barium, allows identification of the zeolite(s) contained in the adsorbent.

Hybrid Process for Producing Paraxylene

Separation Step via Adsorption

The invention relates to a process for producing high-purity paraxylene from a feedstock of aromatic hydrocarbons containing isomers having 8 carbon atoms, by means of an adsorption step A), followed by a crystallization step B), each of the two steps using the same toluene solvent, the adsorption step comprising the following steps:

A1) contacting the feedstock, under suitable adsorption conditions, with a bed of adsorbent such as previously described, in order to selectively adsorb paraxylene;

A2) contacting the bed of adsorbent, under desorption conditions, with a desorbent, or desorption solvent, which is toluene;

A3) withdrawing, from the bed of adsorbent, a stream of raffinate containing the desorbent and the feedstock products the least selectively adsorbed;

A4) withdrawing, from the bed of absorbent, a stream of extract containing the desorbent and paraxylene;

A5) separating the stream of raffinate obtained at step A3) into a first stream containing the desorbent and a second stream containing the feedstock products the least selectively adsorbed; and A6) separating the stream of extract obtained at step A4) into a first stream containing the desorbent and a second stream containing paraxylene having purity equal to or higher than 75%, preferably higher than 85%.

The performance of zeolitic adsorbents such as previously described for the paraxylene separation process in terms of paraxylene purity in the extract and in terms of process yield, is also impacted by the different parameters of the process, namely operating conditions, composition of the feedstock, water content and type of desorbent.

The desorption solvent, also called desorbent, used in the process of the invention is toluene, or more specifically a solvent mostly consisting in toluene i.e. consisting in toluene and possible traces of other C8 components.

The separation step of para-xylene via simulated counter-current adsorption is conducted in accordance with the state of the art which is well known and comprises at least four zones and possibly five or six, each of these zones being constituted by a certain number of successive beds, and each zone being defined by its position comprised between a feed point and a withdrawal point. Typically, a separation unit of paraxylene via simulated counter-current adsorption is fed with at least one feedstock to be fractionated (containing paraxylene and other aromatic C8 isomers) and a desorbent, sometimes called eluent or desorption solvent, and from said unit there is withdrawn at least one raffinate which contains desorbent and the isomers of paraxylene, and an extract which contains paraxylene and desorbent.

The operating conditions of an industrial simulated counter-current adsorption unit using zeolitic adsorbents such as previously described, are typically the following:

number of beds comprised between 4 and 24, preferably between 8 and 12;

number of zones: at least 4;

temperature 100° C. to 250° C., preferably 150° C. to 180° C.;

pressure comprised between toluene bubble point pressure at processing temperature and 3 MPa;

cycle time, corresponding to the time interval between two injections of desorbent into a given bed: comprised between 4 and 18 min;

ratio of desorbent to feed flow rates: 0.7 to 2.5;

recycle ratio (ratio between the mean flow rate of the zones, weighted for the number of beds in each zone, and the feed flow rate): 2 to 12, preferably 2.5 to 4.

The water content in the hydrocarbon effluents is preferably adjusted to between 20 ppm and 150 ppm for a processing temperature in the range of 150° C. to 180° C., to obtain optimal productivity results.

Crystallization Step

The crystallization step is advantageously conducted in a crystallizer and consists in crystallizing the paraxylene derived from the purified stream of the adsorption step containing paraxylene having purity equal to or higher than 75% and ranging up to 98%. The crystallization step makes it possible to obtain firstly paraxylene crystals impregnated with their mother liquor, and secondly a mother liquor which can be partly or even fully recycled by mixing with fresh feedstock at the input to the simulated moving bed adsorption unit.

The crystallization step also comprises washing of the crystals leaving the crystallizer, after which paraxylene is recovered having purity of at least 99.3%, preferably at least 99.7% and more preferably at least 99.8%.

For a purified stream leaving the adsorption unit and entering the crystallization step, and preferably containing from 85 to 90% paraxylene, the temperature of the crystallizer is comprised between 0 and −25° C., preferably between −5° C. and −15° C., and the wash ratio for washing the crystals is generally comprised between 0.8 and 2 volumes of toluene per volume of paraxylene crystals.

The washing solvent of the crystals used in the process of the invention is the same as the solvent used as desorbent in the adsorption unit, namely toluene or a solvent mostly consisting in toluene i.e. consisting in toluene and possible traces of other C8 components, in particular traces of metaxylene.

The streams of desorbent derived from steps A5) and A6) described above are advantageously used at the crystallization step to carry out washing of the crystals. Impure toluene leaving the crystallizer is returned to the above-described step A5) as is the stream of raffinate of the adsorption step. It is also possible to use additional toluene as the washing solvent.

Preferably, one advantageous combination of the invention to produce high-purity paraxylene while reducing costs, and operating costs in particular, consists in combining an SMB-type liquid chromatography separation step in a single adsorption unit containing a reduced number of beds, typically between 8 and 12, with a crystallization step operating at a temperature comprised between −5° C. and 15° C., using toluene both as desorption solvent in the SMB and as washing solvent at the crystallization step.

Technique for Characterization of Zeolites Used and the Lattice Parameters Thereof Measurement of lattice parameter «a» allows identification of the zeolite(s) contained in the adsorbent.

The zeolites present in the adsorbent and their lattice parameter are characterized by X-ray diffraction known to skilled persons as XRD. This analysis is performed using Panalytical apparatus on a sample of zeolitic adsorbent previously ground and screened (fraction smaller than 50 µm). The sample is saturated with water so that it remains stable throughout analysis. For this purpose, the sample is dried at 110° C. in an oven then placed in thin layer in an enclosure having relative humidity of 55% and at ambient temperature for a minimum time of 48 hours.

Analysis is carried out by adding an internal standard (5% silicon with certified lattice parameter) over an angle range (in °2θ) of 5 to 72 °2θ with an angle pitch (in °) of 0.02°. Data are processed with TOPAS refinement software to obtain accurate measurement of the lattice parameter of the zeolites contained in the adsorbent (to within ±0.005 Å).

For a cubic crystalline system, as is the case with the FAU-structure zeolite, the dimensions of the crystal lattice in the 3 directions in space are identical and therefore defined by a single value of the lattice parameter «a». In TOPAS software, the peaks of the diffractogram are modelled by a function of Pseudo-Voigt type, and the background by a polynomial function.

In case several FAU zeolites are present in the adsorbent, this fact is detected by XRD and can be seen in the diffractogram as the presence of peak splitting, particularly visible in the angle range (in °2θ) of 34 to 45 °2θ. For mixtures of FAU zeolites, the split peak selected to define the majority zeolite in the adsorbent is the peak corresponding to 35°±0.6 °2θ, the left peak corresponding to the peak of the zeolite having the largest lattice parameter (i.e. LSX having a lattice parameter of between 25.18 and 25.23 Å in the adsorbents of the examples). By majority zeolite in the adsorbent it is meant the zeolite contributing 50% or more in terms of surface area to the total intensity of the split peak. If needed, and to improve the accuracy of determination of the contribution of each zeolite, a peak deconvolution method can be applied.

The outer surface area of the adsorbent is usually determined by measuring the adsorption isotherm of a gas such as nitrogen, at its liquefaction temperature.

Prior to adsorption, the zeolitic adsorbent is degassed at between 300° C. and 450° C. for a time comprised between 9 hours and 16 hours under vacuum (P<6.7×10$^{-4}$ Pa). Measurement of the nitrogen adsorption isotherm at 77 K is performed on apparatus of Micromeritics type ASAP 200 M, taking at least 35 measurement points at relative pressures of ratio P/PO between 0.002 and 1. The outer surface area is determined by the t-plot method from the isotherm obtained, by applying standard ISO 15901-3:2007 and calculating statistical thickness t with the Harkins-Jura equation. The outer surface area is obtained by linear regression on the points of the t-plot between 0.45 nm and 0.57 nm, from the slope of linear regression.

The outer surface area is expressed in m$^2$ per gram of anhydrous adsorbent.

EXAMPLES

Example 1 (Comparative)

Chromatography Column Separation Test with Prior Art Adsorbents

Separation tests were conducted using a chromatography column in which the zeolitic solid was packed.

The tested solids were:
A: Adsorbent prepared according to Example 4 in patent FR2903987, containing X-type zeolite exchanged with barium, with measured lattice parameter of 25.025 Å;
B: Y-type zeolite adsorbent exchanged both with barium (45 to 65% of sites) and with potassium (35 to 55% of sites) such as described in patent FR2681066 and such as defined in U.S. Pat. No. 3,558,730, with measured lattice parameter of 24.712 Å.
C: Adsorbent containing a mixture of X-LSX, X being in majority, prepared with a crystal molar ratio LSX/X of 0.54, exchanged with barium according to Example 5 in FR2925367, the measured lattice parameters being 25.034 Å for the X-type zeolite and 25.226 Å for the LSX zeolite. The majority zeolite is therefore the X-type zeolite having a lattice parameter smaller than 25.100 Å.

The temperature for the tests is 163° C. corresponding to the temperature routinely recommended for paraxylene separation via hybrid process combining adsorption and crystallization.

The conducted tests are tests of breakthrough/reverse breakthrough type with feed containing 10% volume of iso-octane (iC8) used as tracer, 45% volume of paraxylene (PX) and 45% volume of metaxylene (MX), with a desorption solvent (desorbent) that is toluene.

the breakthrough test corresponds to the feed injection step into the column initially saturated with desorbent;
the reverse breakthrough test corresponds to the desorbent injection step and is performed at the end of the preceding feed injection step.

Figure 3A:
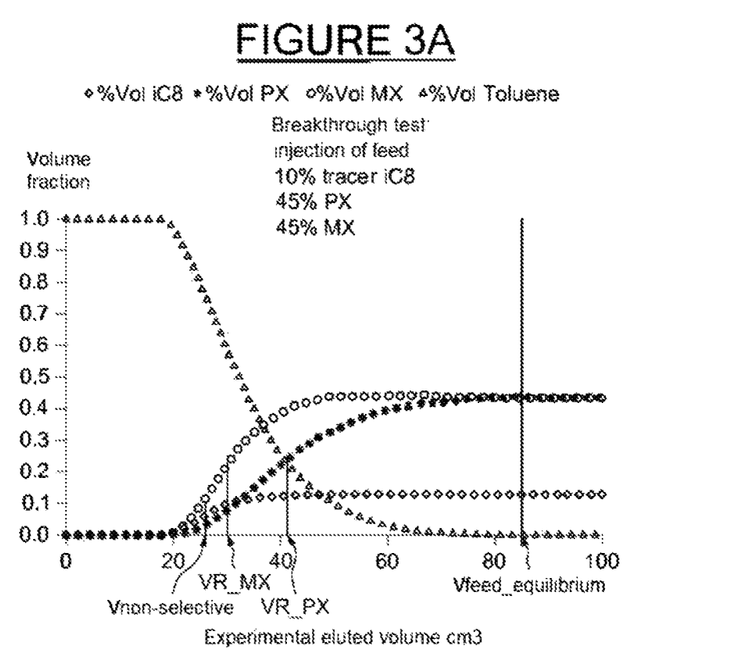
FIGS. 3A and 3B: Breakthrough curves of each compound present in the effluent sampled at the outlet of the chromatographic column, showing changes in the concentrations of each compound as a function of eluted volume, at the breakthrough test (feed injection step) and at the reverse breakthrough test (injection of desorbent), for adsorbent A (BaX).
Figure 3B:
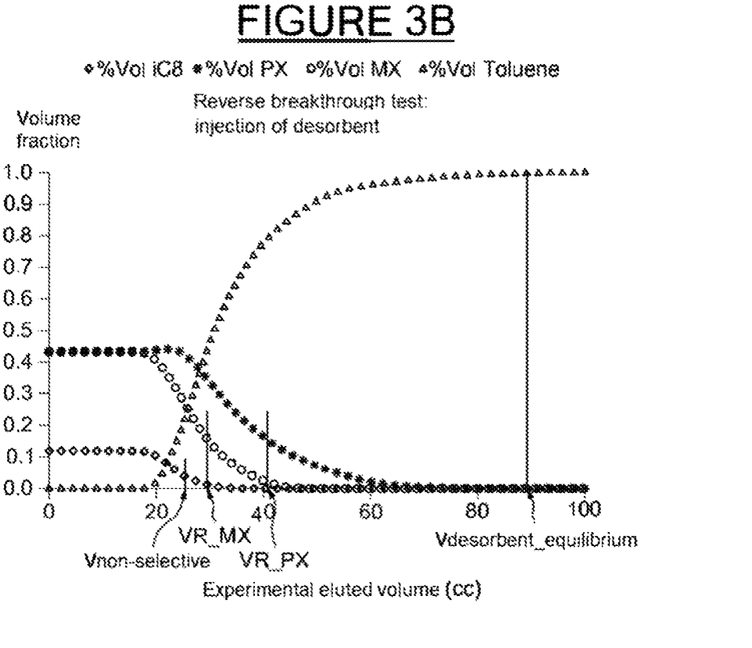

The curves shown in FIGS. 3A and 3B correspond to the breakthrough curves of each compound present in the effluent sampled at the outlet of the chromatography column; they represent the changes in concentrations of each compound as a function of eluted volume at the breakthrough test (feed injection step) and at the reverse breakthrough test (injection of desorbent), for adsorbent A (BaX).

The feed injection step is completed when the concentration of desorbent in the effluent sampled at the outlet of the chromatography column becomes zero i.e. when the composition of the sampled effluent is identical to the composition of the injected feed: the feed volume injected at this point is denoted Vfeed equilibrium and translates the amount of feed that needs to be injected for full saturation of the pore volumes in the column, namely all the non-selective volumes (inter-grain volume and macro and mesopore intra-grain volume) and selective volume (micropore volume of adsorbent).

The iso-octane (iC8) contained in 10% volume in the feed was used as tracer of non-selective volumes (inter-grain volume and macro and mesopore intra-grain volume): measurement of the first instant of the iC8 breakthrough curve therefore gives the estimation of the non-selective volume denoted Vnon selective.

Therefore, by subtracting this non-selective volume from the feed injection volume at equilibrium Vfeed_equilibrium, the necessary feed volume to be injected is obtained in order to saturate the micropore volume Vµ of the adsorbent, namely (Vfeed_equilibrium−Vnon_selective).

Therefore, by multiplying the volume (Vfeed_equilibrium−Vnon-selective) by the fraction xpx of PX contained in the feed, the volume of paraxylene PX to be injected is obtained for the breakthrough test in order to reach adsorption equilibrium in the micropore volume.

Selectivity $\alpha_{PX/MX}$ is the ratio of the adsorbed quantities of PX (paraxylene) and MX (metaxylene) divided by the ratio of PX and MX concentrations in the feed $x_{PX}$ and $x_{MX}$. The adsorbed quantities of PX and MX are obtained starting from the first instants of the PX and MX curves denoted $V_{R\_PX}$ and $V_{R\_NX}$, and from the first instant of the tracer curve giving the non-selective volume denoted Vnon_selective. Therefore, selectivity $\alpha_{PX/MX}$ is calculated with the following equation:

$$\alpha_{PX/MX} = \frac{(V_{R\_PX} - V_{non\_selective})x_{MX}}{(V_{R\_PX} - V_{non\_selective})x_{PX}}$$

Similarly, the desorbent injection step is completed when the concentration of desorbent in the effluent sampled at the outlet of the chromatography column becomes 100%; the volume of desorbent injected at this stage is denoted Vdesorbent_equilibrium and translates the quantity of desorbent that needs to be injected for full regeneration of the pore volumes in the column, namely all the non-selective volumes (inter-grain volume and macro and mesopore intragrain volume) and the selective volume (micropore volume of the adsorbent).

Measurement of the first instant of the iC8 reverse breakthrough curve gives the estimation of the non-selective volume denoted Vnon_selective.

By subtracting this non-selective volume from the desorbent injection volume at equilibrium Vdesorbent_equilibrium, the volume of desorbent to be injected is obtained that is needed for full regeneration of the micropore volume of adsorbent, namely (Vdesorbent_equilibrium−Vnon_selective).

FIGS. 3A and 3B show that for comparative adsorbent A, the volume of desorbent at equilibrium is greater that the volume of feed at equilibrium.

From the breakthrough/reverse breakthrough tests, the ratio $R_{Des/Feed}$ calculated by:

$$R_{Des/Feed}=(V\text{desorbent\_equilibrium}-V\text{non\_selective})/(V\text{feed equilibrium}-V\text{non\_selective})$$

must represent a process similar to the ratio D/F used for separation of paraxylene in a simulated moving bed i.e. the ratio between the desorbent flow rate and the feed flow rate. This parameter translates the quantity of desorbent needed for complete desorbing of the compounds in the feed previously adsorbed in the micropore volume of the adsorbent.

The volume ratios $R_{Des/Feed}$ calculated from the concentration curves of the different compounds for the different tested adsorbents are given in following Table 1:

TABLE 1

Results of breakthrough tests on adsorbents A, B, C in terms of PX/MX selectivity and desorbent/feed volume ratio.

| Comparative | Si/Al of final product | BaO content (wt %) | Measured lattice parameter Å | Comparison of zeolite peaks with lattice parameter >25.100 Å and <25.100 Å | $\alpha_{PX/MX}$ | $R_{Des/Feed}$ |
|---|---|---|---|---|---|---|
| A | 1.25 | 35.2 | 25.025 | | 3.33 | 1.13 |
| B | 2.3 | 10.8 | 24.712 | | 2.55 | 1.29 |
| C | 1.16 | 36.7 | 25.034 (X) and 25.226 (LSX) | X Peak surface area > LSX Peak surface area | 3.65 | 1.03 |

Example 2 (of the Invention)

Tests such as described in Example 1 are conducted on zeolite solids of the invention.

D: Adsorbent prepared according to Example 6 in patent FR2925366 containing LSX zeolite exchanged with barium, with measured lattice parameter of 25.200 Å.

E: Adsorbent comprising at least one FAU-structure zeolite of LSX type comprising barium, with outer surface area measured by nitrogen adsorption of 64 $m^2 \cdot g^{-1}$, prepared according to Example 3 in patent application FR3028430 with measured lattice parameter of 25.204 Å.

F: Adsorbent containing a mixture of X and LSX zeolites (35%-65%), LSX in majority, prepared with a crystal molar ratio LSX/X of 1.86 and exchanged with barium according to Example 5 in patent FR2925367, with measured lattice parameter of 25.031 Å (X) and 25.223 Å (LSX).

G: Adsorbent containing a mixture of X-LSX zeolites, LSX the majority component, prepared with a crystal molar ratio LSX/X of 1, zeolitized and exchanged with barium according to Example 7 of patent FR2925367, with measured lattice parameter of 25.003 Å (X) and 25.181 Å (LSX).

TABLE 2

Results of breakthrough tests on adsorbents D, E, F, G in terms of PX/MX selectivity and desorbent/feed volume ratio.

| Invention | Si/Al of final product | BaO content (wt %) | Measured lattice parameter Å | Comparison of zeolite peaks with lattice parameter >25.100 Å and <25.100 Å | $\alpha_{PX/MX}$ | $R_{Des/Feed}$ |
|---|---|---|---|---|---|---|
| D | 1.03 | 39.3 | 25.200 | | 3.98 | 0.92 |
| E | 1.01 | 33.4 | 25.204 | | 3.03 | 0.89 |
| F | 1.10 | 38.3 | 25.031 (X) and 25.223 (LSX) | LSX Peak surface area > X Peak surface area | 3.75 | 0.93 |
| G | 1.12 | 37.4 | 25.003 (X) and 25.181 (LSX) | LSX Peak surface area > X Peak surface area | 3.65 | 0.98 |

Figure 4:
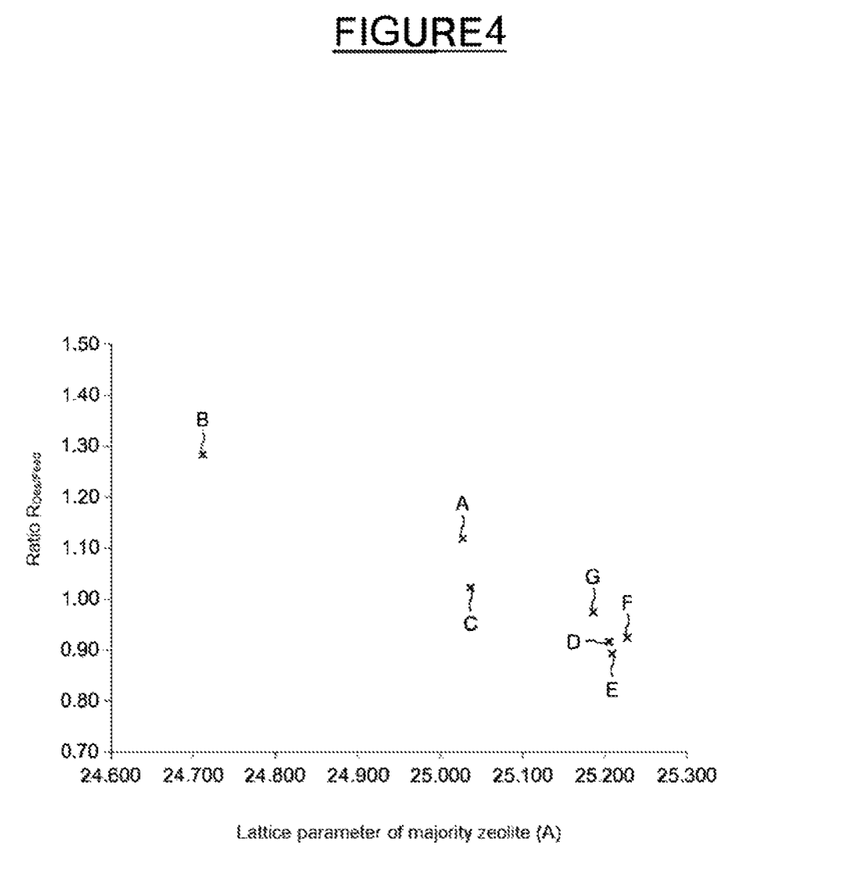
FIG. 4: Graphical representation of the $R_{Des/Feed}$ ratio of the different adsorbents tested in Examples 1 and 2, as a function of the lattice parameter of the majority zeolite.

The volume ratio $R_{Des/Feed}$ of the different adsorbents A to G tested in Examples 1 and 2 are graphically illustrated in FIG. 4 as a function of the lattice parameter of the majority zeolite (LSX).

Example 3 (Comparative)

Breakthrough/reverse breakthrough tests with feed containing 10% by volume of iso-octane used as tracer, 45% by volume of paraxylene PX and 45% by volume of metaxylene MX were conducted on solid D having a lattice parameter conforming to the invention, using a desorbent not conforming to the invention namely para-diethylbenzene (PDEB) and at a temperature of 175° C. routinely recommended when PDEB is used as desorbent.

Table 3 below gives PX/MX selectivity and the volume of injected desorbent corresponding to Vdesorbent_equilibrium i.e. the volume needed so that the concentration of desorbent in the effluent sampled at the outlet of the chromatography column becomes 100%.

TABLE 3

PX/MX selectivity and volume of desorbent at equilibrium as a function of the desorbent used.

| Adsorbent D | Measured lattice parameter Å | $\alpha_{PX/MX}$ | Vdesorbent_equilibrium (cm3) |
|---|---|---|---|
| PDEB at 175° C. (comparative) | 25.200 | 3.89 | 130.5 |
| TOL at 163° C. (invention) | 25.200 | 4.15 | 105.6 |

For one same adsorbent comprising an LSX zeolite having a measured lattice parameter of 25.200 Å and exchanged with barium (adsorbent D), the Vdesorbent_equilibrium volume for the PDEB desorbent at 175° C. is much greater than the Vdesorbent_equilibrium volume for the Toluene desorbent at 163° C. This indicates that the quantity of desorbent needed to desorb the compounds of the feed adsorbed in the micropore volume is much smaller when the toluene solvent is used with adsorbent D.

TABLE 4

Figure 1A:
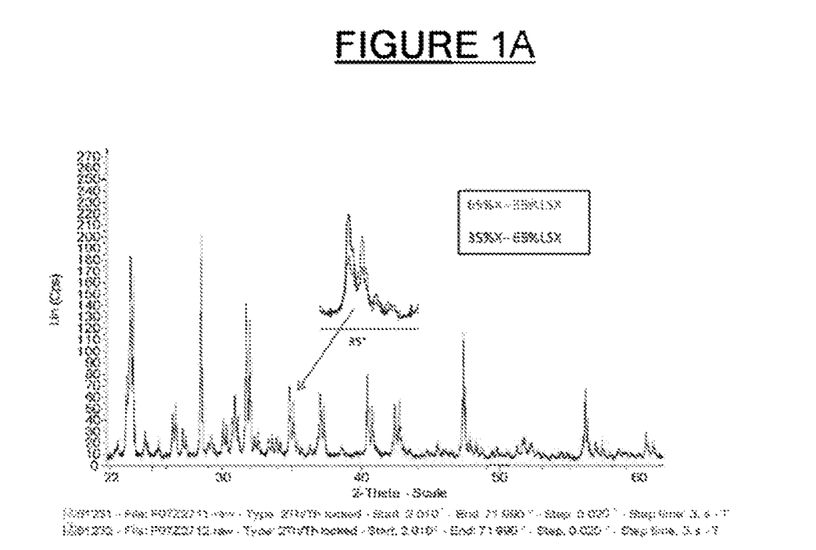
Figure 1B:
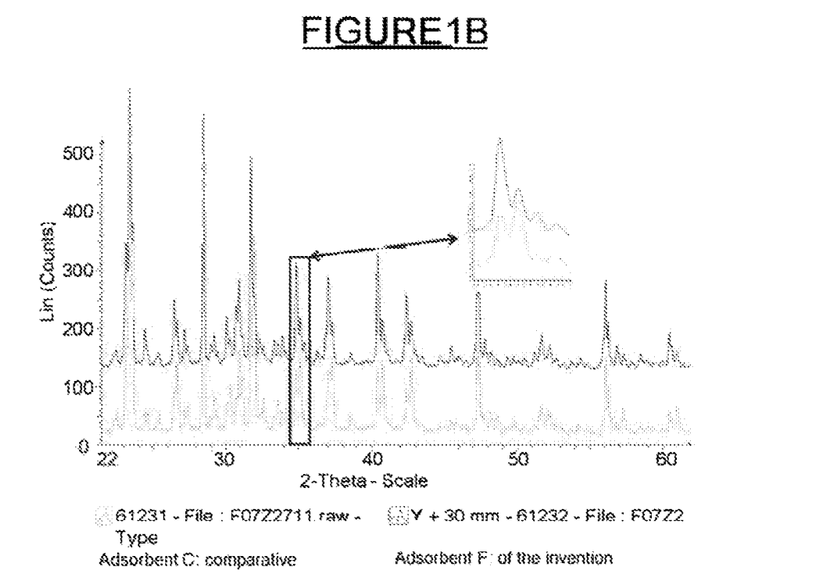
Figure 2:
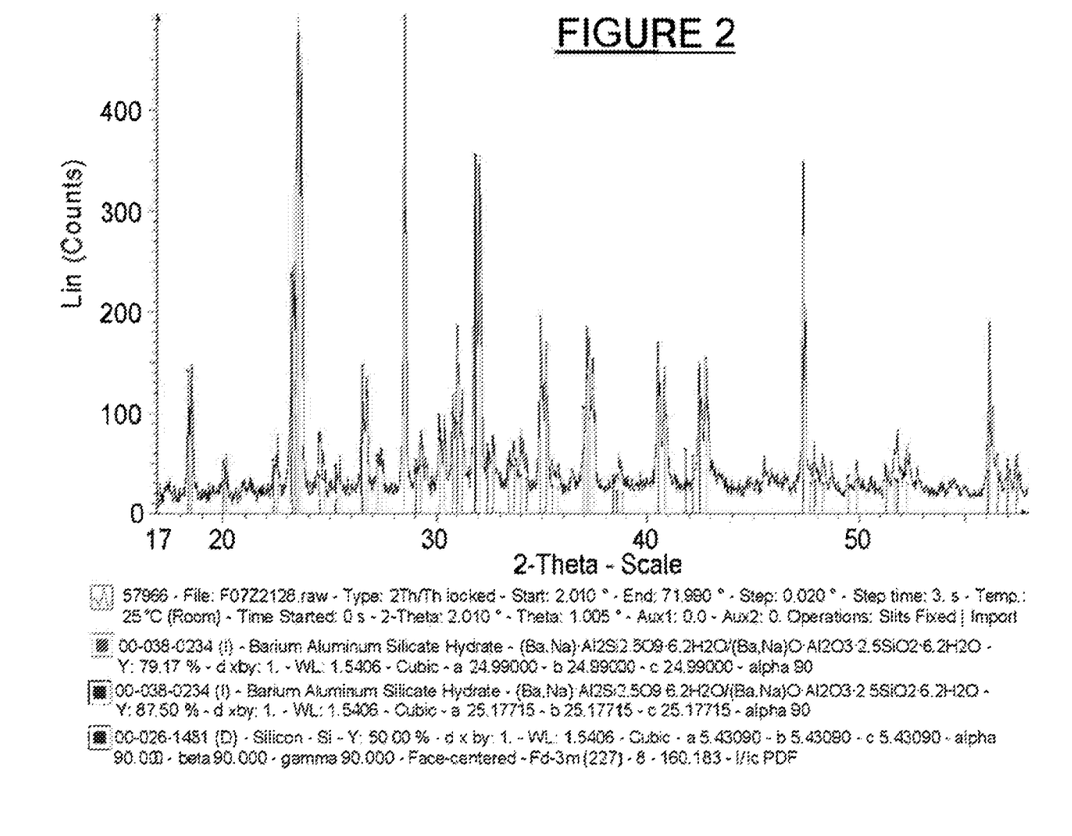
FIG. 2: Diffractogram obtained with X-ray diffraction on adsorbent G (conforming to the invention).

Table of the positions and intensities of the main rays corresponding to the diffractograms in FIGS. 1A, 1B and 2 of adsorbents C, F and G (values of the split peak at 35° shown in bold type).

| Adsorbent C, comparative | | Adsorbent F, invention | | Adsorbent G, invention | |
|---|---|---|---|---|---|
| Angle 2-Theta° | Intensity Count | Angle 2-Theta° | Intensity Count | Angle 2-Theta° | Intensity Count |
| 6.10 | 447 | 6.08 | 527 | 6.12 | 431 |
| 11.67 | 39 | 11.65 | 47 | 11.93 | 72 |
| 12.22 | 370 | 12.16 | 377 | 12.23 | 418 |
| 14.04 | 146 | 14.04 | 220 | 14.08 | 191 |
| 14.12 | 155 | | | | |
| 15.43 | 57 | 15.32 | 43 | 15.34 | 53 |
| 18.29 | 84 | 18.27 | 90 | 18.30 | 93 |
| 18.41 | 140 | 18.40 | 92 | 18.44 | 136 |
| 23.14 | 169 | 23.12 | 234 | 23.18 | 236 |
| 23.35 | 371 | 23.38 | 503 | 23.44 | 462 |
| 23.56 | 429 | 23.56 | 269 | 23.60 | 420 |
| 24.46 | 58 | 24.45 | 84 | 24.50 | 81 |
| 26.45 | 94 | 26.43 | 135 | 26.49 | 109 |
| 26.63 | 146 | 26.64 | 101 | 26.67 | 126 |
| 27.16 | 61 | 27.14 | 85 | 27.21 | 58 |
| 27.34 | 70 | 27.36 | 55 | 27.41 | 63 |
| 29.20 | 79 | 29.18 | 75 | 29.24 | 77 |
| 30.05 | 75 | 30.05 | 107 | 30.11 | 89 |
| 30.29 | 100 | 30.28 | 68 | 30.34 | 86 |
| 30.70 | 84 | 30.69 | 123 | 30.75 | 104 |
| 30.91 | 165 | 30.90 | 170 | 30.96 | 173 |
| 31.13 | 114 | 31.13 | 75 | 31.17 | 107 |
| 31.72 | 240 | 31.71 | 383 | 31.78 | 322 |
| 31.96 | 362 | 31.95 | 218 | 32.01 | 325 |
| 32.56 | 82 | 32.57 | 56 | 32.64 | 70 |
| 33.56 | 75 | 33.56 | 59 | 33.60 | 65 |
| 33.86 | 58 | 33.90 | 72 | 33.95 | 72 |
| 34.83 | 124 | 34.82 | 199 | 34.89 | 175 |
| 35.10 | 153 | 35.11 | 105 | 35.15 | 151 |
| | | 36.85 | 76 | | |
| 37.02 | 129 | 37.01 | 175 | | |
| 37.11 | 133 | | | 37.10 | 162 |
| 37.29 | 143 | 37.29 | 97 | 37.34 | 138 |
| 40.43 | 128 | 40.43 | 216 | 40.50 | 157 |
| 40.75 | 146 | 40.75 | 101 | 40.80 | 131 |
| 42.36 | 92 | 42.37 | 146 | 42.43 | 139 |
| 42.70 | 151 | 42.70 | 97 | 42.75 | 152 |

The invention claimed is:

1. A process for producing para-xylene from a feedstock of aromatic hydrocarbon isomer fractions having 8 carbon atoms, in a liquid phase, comprising:
   a) a liquid chromatography separation step via simulated counter-current adsorption of para-xylene using a zeolitic adsorbent and a desorption solvent, said adsorbent comprising:

at least 50 weight % of a zeolite of faujasite type having a lattice parameter «a» higher than 25.200 Å, barium such that the content of barium oxide BaO is comprised between 30% and 41% by weight, limits included, relative to the total weight of the adsorbent, to obtain a stream of purified para-xylene;

b) a crystallization step of the para-xylene from the purified stream of para-xylene obtained at the separation step, at a temperature between 0 and −25° C., followed by washing of the crystals with a washing solvent, to obtain the para-xylene, wherein the desorption solvent at the separation step and the washing solvent at the crystallization step comprises toluene.

2. The process for producing para-xylene according to claim 1, wherein the adsorbent comprises an LSX zeolite.

3. The process for producing para-xylene according to claim 2, wherein the outer surface area of said zeolitic adsorbent, measured by nitrogen adsorption, is less than 100 $m^2 \cdot g^{-1}$.

4. The process for producing para-xylene according to claim 1, wherein the adsorbent comprises a mixture of zeolites of faujasite type.

5. The process according to claim 4, wherein the adsorbent comprises a mixture of X-type zeolite and LSX zeolite, the LSX zeolite being in majority.

6. The process for producing para-xylene according to claim 1, wherein the content of barium oxide is between 33 and 41%, limits included.

7. The process for producing para-xylene according to claim 6, wherein the content of barium oxide is between 33 and 38%, limits included.

8. The process according to claim 1, wherein the temperature of the crystallization step is between −5° C. and −15° C.

9. The process according to claim 1, wherein the wash ratio of the crystals is between 0.8 and 2 volumes of toluene per volume of para-xylene crystals.

10. The process according to claim 1, wherein the number of beds at the adsorption separation step is between 4 and 24.

11. The process according to claim 10 wherein the number of beds at the adsorption separation step is between 8 and 12.

12. The process according to claim 1, wherein the adsorption separation step is conducted with a number of beds comprised between 4 and 24 said beds comprised in a number of zones of at least 4, a temperature comprised between 100° C. and 250° C., pressure between toluene bubble point pressure at processing temperature and 3 MPa, a cycle time corresponding to the time interval between two injections of desorbent into a given bed of between 4 and 18 min, a ratio of desorbent flow rate to feed flow rate of 0.7 to 2.5, and a recycle ratio comprised between 2 and 12 wherein the recycle ratio is defined as the ratio between the mean flow rate of the zones, weighted for the number of beds in each zone, and the feed flow rate.

13. The process according to claim 12, wherein the adsorption separation step is conducted at a temperature between 150° C. and 180° C.

14. The process according to claim 12, wherein the adsorption separation step is conducted with a recycle ratio of between 2.5 and 4.

15. The process according to claim 12, wherein the adsorbent is prepared according to the following steps:
   a) mixing the faujasite zeolite crystals in powder form of desired particle size, in the presence of water, with at least one binder containing a clay or mixture of clays comprising at least 80% by weight of zeolitizable clay and optionally a silica source;
   b) forming the mixture obtained at a) to produce aggregates, followed by drying and optionally a screening and/or cyclonic separation step;
   c) calcining the aggregates obtained at b) at a temperature in the range of 500° C. to 600° C.;
   d) optional zeolitization of the binder by contacting the calcined aggregates obtained at step c) with an alkaline basic aqueous solution followed by washing;
   e) ion exchange of the zeolitic aggregates containing LSX zeolite or X and LSX zeolite obtained at c) or d) with barium ions, followed by washing and drying of the product thus treated;
   f) heat activation of the aggregates exchanged at step e).

* * * * *

UNITED STATES PATENT AND TRADEMARK OFFICE
CERTIFICATE OF CORRECTION

PATENT NO. : 11,059,764 B2
APPLICATION NO. : 16/642725
DATED : July 13, 2021
INVENTOR(S) : Catherine Laroche et al.

Page 1 of 1

It is certified that error appears in the above-identified patent and that said Letters Patent is hereby corrected as shown below:

In the Specification

Column 15, Line 2, "a lattice parameter «a» higher than 25.200 Å," should read --a lattice parameter «a » higher than 25.100 Å,--

Signed and Sealed this
Seventh Day of September, 2021

Drew Hirshfeld
*Performing the Functions and Duties of the
Under Secretary of Commerce for Intellectual Property and
Director of the United States Patent and Trademark Office*